United States Patent
König

(10) Patent No.: US 11,327,061 B2
(45) Date of Patent: May 10, 2022

(54) METHOD FOR TESTING A MULTITUDE OF SENSOR DEVICES, PANEL FOR USE IN THE METHOD AND SENSOR COMPONENT PRODUCED BY THE METHOD

(71) Applicant: TDK Corporation, Tokyo (JP)

(72) Inventor: Matthias König, Freising (DE)

(73) Assignee: TDK CORPORATION, Tokyo (JP)

( * ) Notice: Subject to any disclaimer, the term of this patent is extended or adjusted under 35 U.S.C. 154(b) by 390 days.

(21) Appl. No.: 16/257,496

(22) Filed: Jan. 25, 2019

(65) Prior Publication Data

US 2019/0234919 A1 Aug. 1, 2019

(30) Foreign Application Priority Data

Jan. 30, 2018 (DE) ...................... 10 2018 102 034.1

(51) Int. Cl.
*G01N 33/00* (2006.01)

(52) U.S. Cl.
CPC ....... *G01N 33/0006* (2013.01); *G01N 33/007* (2013.01); *G01N 33/0016* (2013.01); *G01N 33/0075* (2013.01); *G01N 2033/0072* (2013.01)

(58) Field of Classification Search
CPC .......... G01N 33/0006; G01N 33/0016; G01N 33/007; G01N 33/0075; G01N 2033/0072; G01N 33/0029; G01N 33/0031
USPC ........ 324/663–676, 684–694, 705, 713, 720, 324/721, 722; 73/1.02, 1.06, 1.07, 23.2, 73/23.21, 23.31–23.33, 23.34, 73/31.01–31.03, 31.05, 31.06, 73/114.71–114.73; 338/34, 35; 361/279, 361/280
See application file for complete search history.

(56) References Cited

U.S. PATENT DOCUMENTS

| | | | |
|---|---|---|---|
| 9,818,656 B1 | 11/2017 | Schlarmann et al. | |
| 2003/0037590 A1 | 2/2003 | Stark | |
| 2013/0311108 A1* | 11/2013 | Stetter | A61B 5/0205 702/22 |

(Continued)

FOREIGN PATENT DOCUMENTS

| | | |
|---|---|---|
| DE | 19845112 C2 | 12/2000 |
| EP | 3124962 A1 | 2/2017 |

OTHER PUBLICATIONS

Ams datasheet "AS-MLV-P2 Air Quality Sensor" [v1-01] Oct. 12, 2015, 24 pages.

*Primary Examiner* — Robert R Raevis
(74) *Attorney, Agent, or Firm* — Slater Matsil, LLP

(57) ABSTRACT

A method for testing a plurality of sensor devices, a panel and a sensor component are disclosed. In an embodiment a method includes providing the plurality of sensor devices, each sensor device including a sensor element configured to sense an ambient condition, a heating element to heat the sensor element, connection terminals for a supply voltage and at least one connection terminal for a sense signal indicative of a state of the sensor element, providing a panel including a plurality of groups of connection pads, the connection pads of each one of the groups configured to be connected to the connection terminals of one of the sensor devices, mounting the sensor devices to the groups of connection pads, applying a supply voltage to the sensor devices and concurrently heating the heating elements of the sensor devices to an elevated temperature and calibrating the sensor devices at least one after another.

13 Claims, 3 Drawing Sheets

(56) References Cited

U.S. PATENT DOCUMENTS

| | | | | |
|---|---|---|---|---|
| 2018/0003660 A1* | 1/2018 | Tayebi | ............... | G01N 33/0006 |
| 2018/0038825 A1* | 2/2018 | Ratto | ................... | G01N 27/125 |
| 2019/0346406 A1* | 11/2019 | Gerber | ................... | H01L 43/06 |
| 2021/0015399 A1* | 1/2021 | Gouma | ................ | A61B 5/4884 |

* cited by examiner

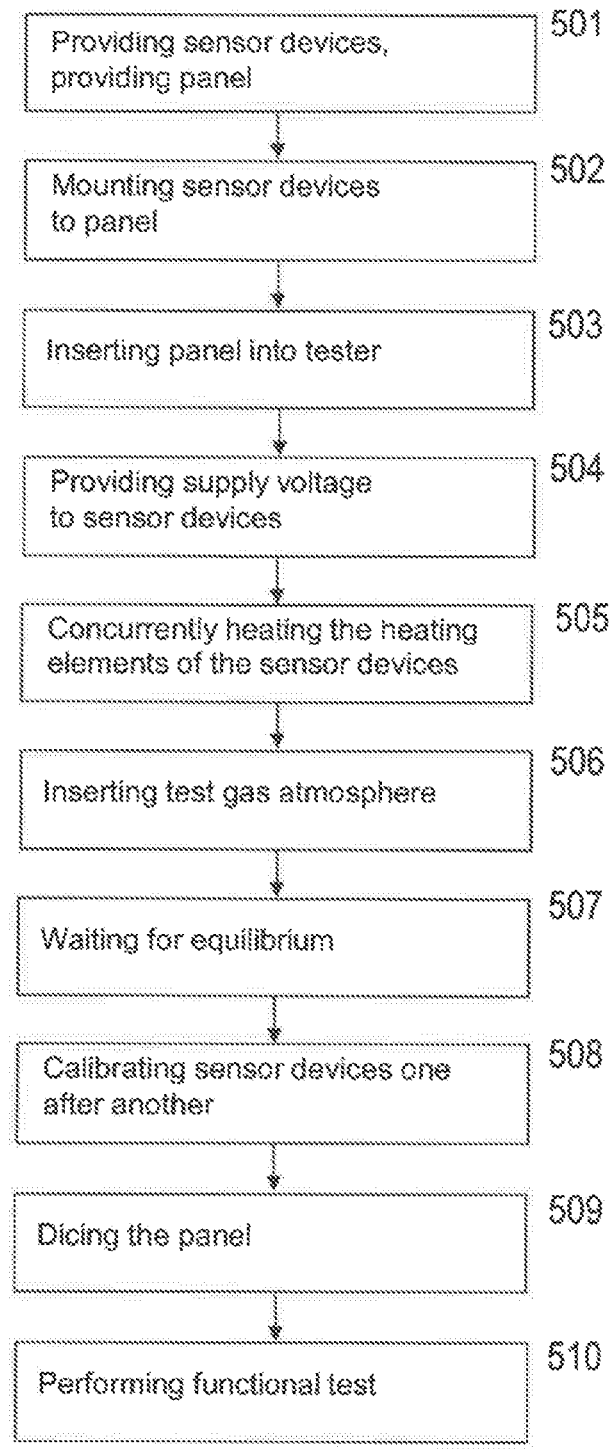

METHOD FOR TESTING A MULTITUDE OF SENSOR DEVICES, PANEL FOR USE IN THE METHOD AND SENSOR COMPONENT PRODUCED BY THE METHOD

This application claims the benefit of German patent application 102018102034.1, filed on Jan. 30, 2018, which application is hereby incorporated herein by reference.

TECHNICAL FIELD

The present disclosure relates to a method for testing a multitude of sensor devices. Specifically, the present disclosure relates to a method for testing a multitude of sensor devices, wherein each sensor device comprises a sensor element configured to sense an ambient condition and a heating element to heat the sensor element. The sensor devices are each equipped with connection terminals for supply voltage and sense signal. The present disclosure also relates to a panel that can be used in the method. This disclosure also relates to a sensor component that is achieved by performing the method.

BACKGROUND

Sensor devices may include heated metal oxide layers that are designed to measure the presence or the concentration of a specific target gas. The gas performs a chemical reaction such as an oxidation on the surface of the heated metal oxide layer. The electrodes generated or required by the chemical reaction cause a change of the impedance of the metal oxide layer that can be determined and evaluated to produce an output signal that is indicative of the concentration of the target gas.

At the end of the production process of the sensor device the sensor should undergo calibration and functional test procedures to meet the expected specifications and accuracy ranges. However, the metal oxide sense elements within the sensor devices may have adsorbates on their surface or may still be covered with substances resulting from the production process. For example, the sensor elements may be covered with water molecules that are always present in ambient air and solvents that originate from the production process of the metal oxide layers or with other contaminants.

While it usually takes a short time to heat up the sensor elements, it requires a considerably longer time for the adsorbates and the solvents to evaporate from the heated sensor elements. In order to obtain a good calibration result, the sensor element should have achieved the equilibrium state at elevated temperature before the calibration procedure begins. For a typical metal oxide gas sensor, the heating time may be in the range of about 1 second (typically 20 milliseconds to 1 second), whereas the time to achieve the equilibrium may last from about 1 to 30 minutes. In a common tester that tests one sensor device after the other, it is commercially almost impossible to wait for the sensor to achieve the equilibrium state because the throughput would be drastically low and the calibration process would be rather expensive. Present sensor devices that operate with a metal oxide sensor element at elevated temperature are only purely calibrated or are even sold uncalibrated.

SUMMARY

Embodiments provide a method for testing and calibrating sensor devices that employ the principle of heated metal oxide sensor layers that has a high throughput rate and achieves a good calibration result.

Embodiments provide a method for testing a multitude of sensor devices that has a high throughput rate and provides a good calibration result.

Embodiments provide an equipment with which a multitude of sensor devices can be tested at a high throughput rate and to ensure a good calibration result.

Embodiments provide a sensor device that is treated by the multi-testing procedure.

In an embodiment of the present disclosure, a method for testing a multitude of sensor devices comprises: providing a multitude of sensor devices, each sensor device comprising a sensor element configured to sense an ambient condition, a heating element to heat the sensor element, connection terminals for a supply voltage and at least one connection terminal for a sense signal indicative of the state of the sensor element; providing a panel, the panel comprising a multitude of groups of connection pads, the connection pads of each one of the groups configured to be connected to the connection terminals of one of the sensor devices; mounting the sensor devices to the groups of connection pads; applying a supply voltage to the sensor devices and concurrently heating the heating elements of the sensor devices to an elevated temperature; calibrating the sensor devices at least one after another.

In an embodiment the disclosed method is directed to sensor devices that have a heated sensor element, wherein the sensor element is configured to sense an ambient condition such as a concentration of a specific gas or humidity in various environments. Typical fields of application include industry, high temperature processing, automotive, air conditioning, mobile and the medical sector. The heating of the gas sensor is achieved by a resistive heating element that is biased by a heating current. For test and calibration, the multitude of sensor devices is placed on a panel that is suitably equipped with connection pads and wires so that a supply voltage can simultaneously be supplied to the multitude of sensor devices so that the devices can concurrently heat up to the elevated temperature and wait concurrently until the equilibrium state is achieved. Then, the tester can proceed and calibrate one sensor device after the other or a subgroup of sensor devices after the other. The time-consuming process of heating and achieving the equilibrium state is performed in parallel and simultaneously for the multitude of sensor devices, while the subsequent calibration process is relatively fast and can be performed individually. The throughput is increased in that the time-consuming part of the testing procedure is performed concurrently for a great number of sensor devices.

In embodiments, during the application of the supply voltage and the parallel heating of the sensor devices, a test gas atmosphere is inserted into the closed chamber of the tester. The test gas atmosphere has a well-defined concentration. The test gas atmosphere comprises that target gas for the measurement of which the sensor is dedicated.

In order to achieve the equilibrium state, the elevated temperature of the sensor element causes the contaminants to disappear such as adsorbed water vapor and/or solvents that are left over from the manufacturing process of the heating element. In the equilibrium state, the solvents disappeared and the water vapor has achieved an equilibrium of desorption and adsorption.

The testing procedure may then proceed with the calibration of the sensor devices, wherein usually one sensor device is calibrated after the other, which is acceptable because the calibration procedure is relatively fast. For calibration, the tester may receive a signal from the sensor element and compare it with a predetermined value that represents the concentration of the test gas in the test gas atmosphere. The comparison will deliver at least one correction value that is required to correct the sensing characteristic of the sensor element so that the combination of correction value and sense signal indicates the proper test gas concentration.

The correction value may be stored in an application-specific integrated circuit (ASIC) that is incorporated in the package of the sensor device. Such an ASIC may be responsible for generating the adequate heating current from the supply voltage, perform a measurement at the sensor device and perform suitable evaluations to provide an output signal that is indicative of the result of the measurement such as the concentration of the target gas in the ambient atmosphere. The measurement may be a resistance measurement detecting the change of the resistance of the metal oxide layer in response to the test gas atmosphere. Other measurements are also possible that generate an output signal in response to changes of resistance, current and/or voltage at the sensor element.

The ASIC may be configured such that it determines that a supply voltage is applied for the first time to the sensor device. This is an indicator for the fact that the test and calibration procedure starts so that the sensor device automatically goes into the heating mode and heats the heating element automatically. The first time application event may be determined by the status of the on-chip memory in that the circuit realizes that it is still empty and includes no correction value yet.

While the calibration process may be performed on panel level, the panel may be diced after finishing the calibration process to form individualized sensor components. The diced components are compositions of the sensor device attached to the diced panel piece.

A final functional test may then be performed on the separated compositions to validate the electrical and functional performance of the completed sensor components. The functional test is also performed on an individual basis of one component after the other or of a small group of components after the other. As explained above, the rather time-consuming step of heating the sensor devices and waiting to achieve the equilibrium state is, instead, parallel and simultaneous for a great number of sensor devices.

The sensor devices may be configured to sense the presence or the concentration of a specific target gas, humidity conditions or a medical gas component. Furthermore, sensors can be combinations of gas sensors with other sensors such as pressure sensors. Specifically, the sensor elements of these sensor devices are made of a metal oxide, wherein the metal oxide may be one of tin oxide, indium oxide, gallium oxide or ruthenium oxide, wherein sensor elements made of tin oxide may provide the broadest range of applications. The sensors concerned in the present disclosure may have in common that they need a relatively long time to find the equilibrium state.

The heating elements may be resistive heating wires that may be disposed beneath the sensor elements isolated from the sensor elements by an insulation layer. The heating elements may cover a reasonable area that can be achieved by a meander shape of the heating wire. Specifically, the heating element may be made of a metal from one of tungsten and platinum. The heating element being made of palladium is also possible.

Embodiments provide a panel arrangement for use in the above described method that comprises: a substrate; a multitude of groups of connection pads, the connection pads configured to be connected to corresponding connection terminals of a sensor device; a wire for a supply potential, said wire connected to a respective connection pad in each one of the groups of connection pads; another wire for a ground potential, said other wire connected to another respective connection pad in each one of the groups of connection pads.

The panel arrangement comprises a substrate on which a multitude of sensor devices can be mounted. Connection pads are provided for each of the sensor devices. The ones of the connection pads that are configured to provide the positive supply potential to the sensor devices are connected together to a first wire. The ones of the connection pads that are configured to apply the ground potential to the sensor devices are all connected to another wire. The multitude of sensor devices and the multitude of connection pads may be organized in rows so that two or more rows are disposed on the panel arrangement in parallel fashion. The wires for the supply voltage and for the ground potential may be disposed in one or more layers of the multilayer structure of the panel. The panel may be made of a ceramic material in which multiple metal layers are disposed to supply the supply and ground potentials. In general, the sensor devices that may be disposed on the panel arrangement can be organized in several rows or areas and their connection pads for the supply potential and the ground potential are connected together using the different metal layers within the ceramic substrate of the panel. In one embodiment, all the connection pads for the supply potential may be connected together by the first wire and all the connection pads for the ground potential may be connected together by the second wire so that all sensor elements disposed on the panel arrangement in a calibration process can be heated simultaneously.

After calibration, as explained above, the panel may be diced in order to individualize compositions of sensor device plus the diced panel piece. The dicing process cuts the wires for the supply potential and the ground potential and thereby generates diced sidewall portions of the panel pieces that include the cut surfaces of the wires for the supply and ground potentials. In one embodiment, the cut wires for supply and ground potentials may be included in diced sidewall portions of the panel that are located on opposite sides of the rectangular form of the diced panel piece.

BRIEF DESCRIPTION OF THE DRAWINGS

It is to be understood that both the foregoing general description and the following detailed description are merely exemplary, and are intended to provide an overview or framework to understand the nature and character of the claims. The accompanying drawings are included to provide a further understanding and are incorporated in, and constitute a part of, this description. The drawings illustrate one or more embodiments, and together with the description serve to explain principles and operation of the various embodiments. The same elements in different figures of the drawings are denoted by the same reference signs.

In the drawings:

FIG. 5 shows a flow diagram of the process to calibrate a multitude of sensor devices.

DETAILED DESCRIPTION OF ILLUSTRATIVE EMBODIMENTS

The present disclosure will now be described more fully hereinafter with the reference to the accompanying drawings showing embodiments of the disclosure. The disclosure may, however, be embodied in many different forms and should not be construed as limited to the embodiments set forth herein. Rather, these embodiments are provided so that the disclosure will fully convey the scope of the disclosure to those skilled in the art. The drawings are not necessarily drawn to scale but are configured to clearly illustrate the disclosure.

Figure 1:
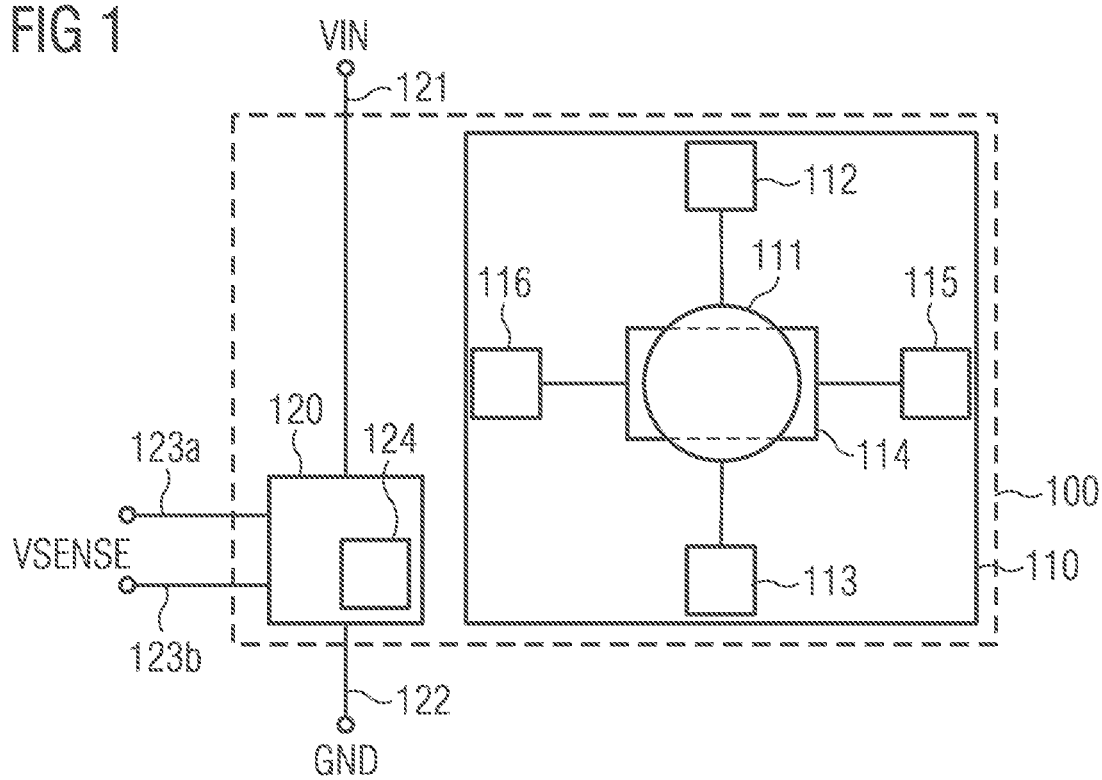
FIG. 1 shows a principle top view on an exemplary sensor device.

FIG. 1 shows a top view on a sensor device 100. Device 100 may be a gas sensor to sense the presence or concentration of a reactive gas such as CO, $CO_2$, $NH_3$, NOx and VOCs (volatile organic compounds). The device includes a substrate 110 that may be silicon dioxide. A metal oxide sensing element 111 is connected to terminals 112, 113 that provide a sensing signal. A heating element 114 is disposed beneath the sensing element 111 and heats the sensing element 111 to an elevated temperature, for example, about 300.degree. C., by the application of an electrical current supplied to terminals 115, 116. An application-specific integrated circuit (ASIC) 120 is also disposed within the sensor device 100. The ASIC 120 is supplied with positive supply potential VIN at terminal 121 and ground potential GND at terminal 122. The ASIC generates the proper supply current to heat the heating element 114 and supplies this heating current to terminals 115, 116. The ASIC provides a regulation of the heating current in a control loop so that the temperature of the heating element 114 is maintained substantially constant. A suitable temperature may be at 300.degree. C. or about 300.degree. C. Depending on the field of application, other temperatures that may reach up to the range of, for example, 800.degree. C. are also possible. The terminals 112, 113 supply a sense signal to the ASIC 120 which generates an output sense signal VSENSE at its terminals 123a, 123b, that is indicative of the sensed gas concentration. Terminals 123a, 123b, may provide a digital signal indicative of the sensed gas concentration. The digital signal can be transmitted by a common bus protocol such as $I^2C$. The terminals of the ASIC 120 such as terminals 121, 122, 123a, 123b, are accessible to the external of the sensor device 100.

The sensing element 111 may be made of a metal oxide such as tin oxide. Other oxides are also useful such as indium oxide, gallium oxide or ruthenium oxide. The heating element 114 may be made of a metal such as tungsten. Other metals are also useful such as platinum or palladium. In operation, the reactive gas interacts with the heated surface of the metal oxide sensor element 111 and may be oxidized. The electrons used in the oxidization process cause a resistance change at terminals 112, 113. The resistance state of the sensor element 111 is evaluated in the ASIC 120 and output to terminals 123a, 123b.

At the end of the fabrication process of sensor device 100, the sensor must be calibrated to meet the expected specifications. However, the metal oxide sensor element 111 may still be contaminated with substances from the manufacturing processes such as solvents that are used to provide the metal oxide particles. Furthermore, water vapor molecules ($H_2O$) may adhere to the sensing element 111 as water vapor is almost everywhere in the ambient gas atmosphere.

The heating up of the sensing element 111 is achieved in a rather fast way in the range of about 20 ms to about 1 s, whereas it takes much longer time to remove the residual solvents and the water steam from the sensing element 111. This process may last for several minutes, up to about 30 minutes. Calibration is only useful when the contaminants have disappeared from the sensing element 111 and the water vapor achieves an equilibrium of adsorption and resorption.

Figure 2:
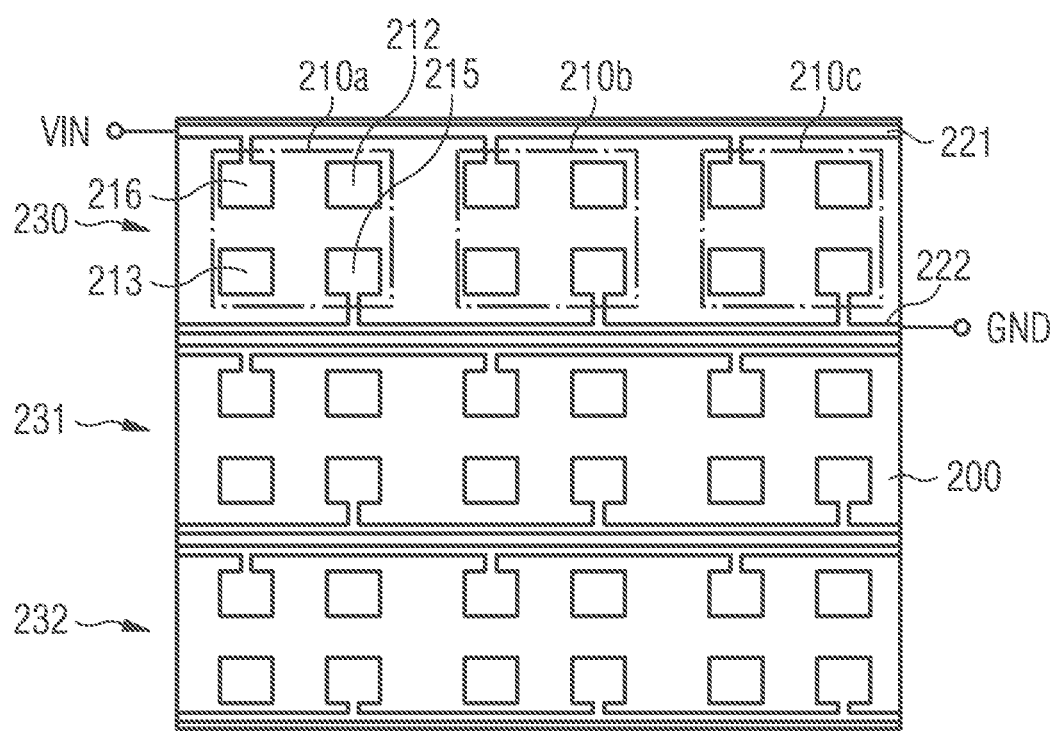
FIG. 2 shows a view onto a panel.
Figure 3:
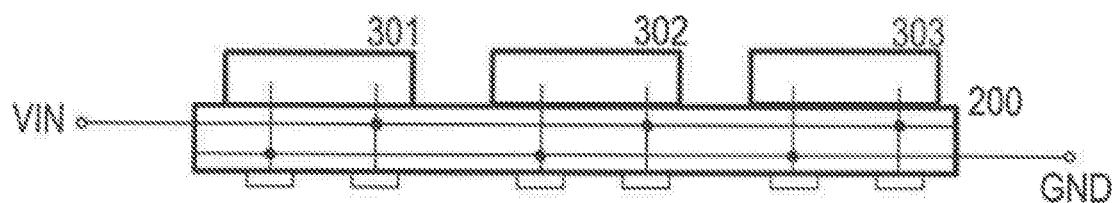
FIG. 3 shows a side view onto a panel on which sensor devices are disposed.

FIG. 2 shows a panel to be used in connection with the present disclosure. Panel 200 may be made of a ceramic basic material and incorporates wires and contact pads made of metal. Contact pads 212, 213, 215, 216 are arranged in a group 210a. A multitude of groups of connection pads including other groups 210b, 210C are disposed on the panel. As shown in the side view of FIG. 3, sensor devices 301, 302, 303 are disposed on corresponding groups of connection pads. For example, the terminals for the supply voltage to generate the heating current and terminals for the sensing signal of the ASIC such as terminals 123a, 123b, 122, 121 (FIG. 1) are connected to the contact pads 212, 213, 215, 216 of the first group 210a of connection pads on panel 200. The groups 210a, 210b, 210C of one row 230 on panel 200 are connected together to wires 221 and 222 which provide a positive supply potential VIN and ground potential GND, respectively. The corresponding connection pads of the groups 210a through 210C such as pad 216 used to supply the positive supply potential VIN to the corresponding terminal 121 of sensor device 100 (or, e.g., 301) are connected to wire 221. In a similar way, the corresponding connection pads of the groups 210a through 210C such as pad 215 used to supply the ground potential to terminal 122 of sensor device 301 are connected to ground potential wire 222. As a result, all sensor devices 301, 302, 303 (or 100) of the first row 230 of panel 200 are connected to the same supply wires 221, 222 to supply positive supply potential VIN and ground potential GND. Also the rows 231, 232 are connected to corresponding wires for positive supply potential VIN and ground potential GND. The supply potential wires of different rows may be connected together so that the full array of the panel 200 may be supplied at the same time with the same supply potential. Other organizations are also possible.

Figure 4:
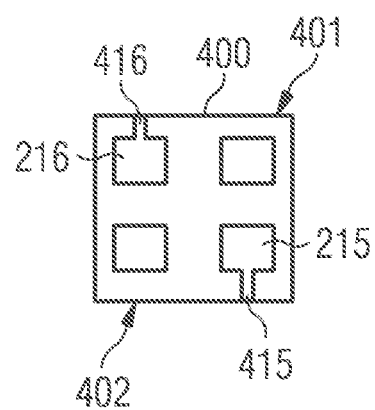
FIG. 4 shows a view onto a diced piece of the panel.

FIG. 4 shows a view on a piece of the panel after dicing. The sensor devices remain combined with the rectangular panel piece 400 that has been diced. The panel piece 400 has four diced sidewalls. Two diced sidewalls 401, 402 that are disposed on opposite ends of the diced panel piece 400 include the cut wires 216, 215 that had lead from the corresponding connection pads 216, 215 to the wires 221, 222 for the supply and ground potentials VIN, GND. The cut surfaces of the metallic connection portions 416, 415 are visible on the diced panel piece sidewall.

After the fabrication of a sensor device and before shipping to the customer, the sensor device should be calibrated so that the output signal VSENSE provides a proper signal that is indicative of the sensed ambient condition such as the gas concentration of a specific reactive gas. The calibration and testing process is depicted in FIG. 5. A multitude of identical sensor devices 100 is provided. Also provided is the ceramic panel 200 including the metallic connection pads and the wires 221, 222 connecting the pads for potential VIN and the pads for ground potential GND (step 501).

Each one of the sensor devices is mounted on the panel and the connection terminals of the sensor devices are matched and connected to corresponding groups of connection pads of the panel 200 (step 502).

The panel 200 equipped with the multitude of sensor devices is inserted into the tester machine. The pins for supplying positive supply potential VIN and ground potential GND are connected to the wires 221 and 222 (step 504).

The multitude of sensor devices is then provided with electrical power so that the ASIC 120 can generate the respective currents to heat the heating elements 114 of each sensor device. Heating is performed concurrently and simultaneously for all the sensor devices in parallel (step 505).

A test gas atmosphere with defined gas concentration is inserted. The test gas atmosphere comprises that gas for which the sensor is to be calibrated and for the measurement of which the sensor is dedicated and configured. The tester has a closed chamber in which the panel is positioned and in which the gas is inserted (step 506).

The process will now wait for a sufficient amount of time so that the contaminants disappear from the metal oxide sensing element 111. Contaminants may be solvents left over from the production of the sensing element 111. Furthermore, water vapor may adhere to the metal oxide sensing element 111 and it takes quite a long time so that surplus water vapor disappears and the sensing element 111 achieves an equilibrium state of adsorption and resorption (step 507). While the heating up of heating element 114 and sensing element 111 may be achieved in a rather short time of several seconds or even about 1 second, the waiting period until the equilibrium state is achieved will last considerably longer. This may require up to several minutes. In the worst case, this can last until expiry of about 30 minutes. Heating and waiting for the equilibrium state is performed in parallel for all of the sensor devices mounted on the panel substrate.

Turning now to step 508, the sensor devices are calibrated. The calibration process can be made for one sensor device after the other in that the probe needles from the tester contact the terminals of the sensor devices and perform the calibration process for that sensor device. If a tester has more probe needles and channels, more than one sensor device can be tested in parallel. Usually, the tester may have only few probe needles and channels so that only a small subset of the multitude of sensor devices on the panel or even one single sensor device can be tested at a time. During the calibration process, the tester evaluates the sense output signal VSENSE in response to the known gas concentration supplied to the chamber of the tester. A correction value is calculated so that the combination of sense value and correction value is a measure for and is indicative of the measured concentration of the test gas. The correction value is applied to the characteristics of the sensor device. The correction value is stored in the ASIC of the chip such as in one time programmable memory 124 (step 508).

After the calibration process has been completed for all of the sensor devices on the panel, the panel will be diced through dicing lines that separate the panel into a multitude of panel pieces comprising the diced portion of the panel combined with the sensor device attached thereto. The sensor component comprising a sensor device plus panel piece can be placed into a package (step 509).

The individual sensor component will then be subjected to a functional test which validates the electrical and logical function of the sensor circuit (step 510).

An advantage of the present disclosure is that the time-consuming portions of the test and calibration procedures are performed in parallel for a multitude of sensor devices so that the average time spent per device is low. On the other hand, the specific calibration and test procedures will be performed for one individual device one after the other, or at best a small group of individual devices one after the other group depending on the capabilities of the tester machine. During the initial steps, the application of supply power, the heating up of the devices, the inserting of the gas atmosphere and the waiting for the equilibrium state are performed in parallel for all devices on the panel. Depending on the field of application of the sensor, the specific test gas atmosphere and the specific temperature to which the sensing element is to be heated may vary.

In an embodiment, the ASIC 120 of the sensor device 100 may be formed such that the ASIC determines that the device is still uncalibrated, for example, in that the programmable memory 124 is empty. In that case the ASIC may go immediately into the heating mode when it realizes that the supply voltage VIN, GND is supplied.

It will be apparent to those skilled in the art that various modifications and variations can be made without departing from the spirit or scope of the disclosure as laid down in the appended claims. Since modifications, combinations, sub-combinations and variations of the disclosed embodiments incorporating the spirit and substance of the disclosure may occur to the persons skilled in the art, the disclosure should be construed to include everything within the scope of the appended claims.

What is claimed is:

1. A method for testing a plurality of sensor devices, the method comprising:
   providing the plurality of sensor devices, each sensor device comprising a sensor element configured to sense an ambient condition, a heating element configured to heat the sensor element, connection terminals for a supply voltage and at least one connection terminal for a sense signal indicative of a state of the sensor element;
   providing a panel, the panel comprising a plurality of groups of connection pads, the connection pads of each one of the groups configured to be connected to the connection terminals of one of the sensor devices;
   mounting the sensor devices to the groups of connection pads;
   applying a common supply voltage to the terminals for the supply voltage of the sensor devices and concurrently heating the heating elements of the sensor devices to an elevated temperature; and
   calibrating at least one or more of the sensor devices at a time.

2. The method according to claim 1, further comprising subjecting the sensor devices to a test gas atmosphere after providing the supply voltage to the sensor devices.

3. The method according to claim 2, wherein subjecting the sensor devices to the test gas atmosphere comprises waiting a predetermined amount of time until the sensor elements of the sensor devices achieve an equilibrium state.

4. The method according to claim 2, wherein calibrating the sensor devices comprises:
   receiving a respective signal from a sensor element of one of the sensor devices;
   comparing the signal with a predetermined value; and
   storing a correction value in a respective memory disposed in the one of the sensor devices.

5. The method according to claim 4, wherein the predetermined value is indicative of a concentration of the test gas atmosphere and the correction value is set such that a combination of the signal from the sensor element and the correction value is indicative of the concentration of the test gas atmosphere.

6. The method according to claim 1, further comprising, after calibrating the sensor devices:

dicing the panel to obtain individualized sensor components; and performing a functional test on the sensor devices in the individualized sensor components.

7. The method according to claim 1, wherein providing the plurality of sensor devices comprises providing the sensor devices that are configured to heat the heating element automatically in response to an application of the supply voltage.

8. The method according to claim 1, wherein the sensor element comprises a metal oxide from the group consisting of tin oxide, indium oxide, gallium oxide and ruthenium oxide, and wherein the heating element comprises a metal from the group consisting of tungsten, platinum and palladium.

9. The method according to claim 1, wherein the plurality of groups is arranged in rows and columns on the panel.

10. The method according to claim 9, wherein the sensor devices of a row of the panel are connected to the same positive supply line and the same negative supply line.

11. The method according to claim 10, wherein supply lines of different rows are connected together such that the positive supply lines of all rows are connected together and the negative supply lines of all rows are connected together.

12. The method according to claim 1, wherein the sensor element comprises a metal oxide from the group consisting of tin oxide, indium oxide, gallium oxide and ruthenium oxide.

13. The method according to claim 1, wherein the heating element comprises a metal from the group consisting of tungsten, platinum and palladium.

* * * * *